US011413177B2

(12) United States Patent
Lostetter

(10) Patent No.: US 11,413,177 B2
(45) Date of Patent: Aug. 16, 2022

(54) STENT GRAFT DELIVERY SYSTEM WITH CONSTRICTED SHEATH AND METHOD OF USE

(71) Applicant: Bolton Medical, Inc., Sunrise, FL (US)

(72) Inventor: Timothy Lostetter, Sunrise, FL (US)

(73) Assignee: Bolton Medical, Inc., Sunrise, FL (US)

(*) Notice: Subject to any disclaimer, the term of this patent is extended or adjusted under 35 U.S.C. 154(b) by 210 days.

(21) Appl. No.: 16/391,995

(22) Filed: Apr. 23, 2019

(65) Prior Publication Data
US 2019/0247213 A1 Aug. 15, 2019

Related U.S. Application Data

(63) Continuation of application No. PCT/US2018/019354, filed on Feb. 23, 2018.
(Continued)

(51) Int. Cl.
*A61F 2/95* (2013.01)
*A61F 2/97* (2013.01)
(Continued)

(52) U.S. Cl.
CPC .................. *A61F 2/97* (2013.01); *A61F 2/07* (2013.01); *A61M 25/09041* (2013.01);
(Continued)

(58) Field of Classification Search
CPC ........ A61F 2/97; A61F 2/07; A61F 2002/061; A61F 2002/9534; A61F 2002/9665;
(Continued)

(56) References Cited

U.S. PATENT DOCUMENTS

| 5,123,917 A | 6/1992 | Lee |
| 5,242,452 A | 9/1993 | Inoue |

(Continued)

FOREIGN PATENT DOCUMENTS

| CN | 105832447 A | 8/2016 |
| EP | 1847234 A1 | 10/2007 |

(Continued)

OTHER PUBLICATIONS

International Preliminary Report on Patentability for International Application No. PCT/US2018/019354 dated Aug. 27, 2019.
(Continued)

*Primary Examiner* — Erich G Herbermann
(74) *Attorney, Agent, or Firm* — Foley Hoag LLP

(57) ABSTRACT

A delivery system and method for implanting a stent graft includes a flexible sheath that defines openings distributed longitudinally and wherein substantial alignment of the openings along a longitudinal axis of a guidewire catheter radially constrict the flexible sheath. The flexible sheath includes at least one fenestration. A ligature extends through the openings of the flexible sheath and causes the openings to be substantially aligned, thereby constraining the flexible sheath. The ligature is proximally retractable from the openings to thereby release the flexible sheath from a radially constricted configuration.

12 Claims, 9 Drawing Sheets

Related U.S. Application Data

(60) Provisional application No. 62/463,051, filed on Feb. 24, 2017.

(51) Int. Cl.
 *A61F 2/07* (2013.01)
 *A61M 25/09* (2006.01)
 *A61F 2/06* (2013.01)
 *A61F 2/966* (2013.01)

(52) U.S. Cl.
 CPC . *A61F 2002/061* (2013.01); *A61F 2002/9534* (2013.01); *A61F 2002/9665* (2013.01); *A61F 2210/0014* (2013.01); *A61F 2220/0075* (2013.01)

(58) Field of Classification Search
 CPC ...... A61F 2210/0014; A61F 2220/0075; A61F 2/2436; A61F 2/2439; A61F 2/962; A61F 2/966; A61F 2/95; A61F 2/9522; A61F 2/954; A61F 2002/9623; A61F 2002/9528; A61F 2002/9505; A61F 2002/9511; A61F 2002/9583; A61M 25/09041; B21D 39/04; B21D 39/046
 See application file for complete search history.

(56) References Cited

U.S. PATENT DOCUMENTS

| | | | |
|---|---|---|---|
| 5,507,769 A | 4/1996 | Marin et al. | |
| 5,755,769 A * | 5/1998 | Richard | A61F 2/90 623/1.2 |
| 5,873,906 A | 2/1999 | Lau et al. | |
| 6,113,623 A | 9/2000 | Sgro | |
| 6,171,334 B1 | 1/2001 | Cox | |
| 6,280,464 B1 | 8/2001 | Hayashi | |
| 6,395,018 B1 | 5/2002 | Castaneda | |
| 7,435,253 B1 | 10/2008 | Hartley et al. | |
| 7,637,940 B2 | 12/2009 | Kocur et al. | |
| 7,763,063 B2 | 7/2010 | Arbefeuille et al. | |
| 8,007,605 B2 | 8/2011 | Arbefeuille et al. | |
| 8,062,345 B2 | 11/2011 | Ouellette et al. | |
| 8,172,895 B2 | 5/2012 | Anderson et al. | |
| 8,236,040 B2 * | 8/2012 | Mayberry | A61F 2/97 623/1.11 |
| 8,480,725 B2 | 7/2013 | Rasmussen et al. | |
| 8,486,129 B2 | 7/2013 | Lautherjung | |
| 8,500,792 B2 | 8/2013 | Berra | |
| 8,641,752 B1 | 2/2014 | Holm et al. | |
| 8,808,351 B2 | 8/2014 | Osborne | |
| 8,926,693 B2 | 1/2015 | Duffy et al. | |
| 9,101,455 B2 | 8/2015 | Roeder et al. | |
| 9,101,506 B2 | 8/2015 | Arbefeuille et al. | |
| 9,259,336 B2 | 2/2016 | Schaeffer et al. | |
| 9,364,314 B2 | 6/2016 | Berra et al. | |
| 9,375,308 B2 | 6/2016 | Norris | |
| 9,439,751 B2 | 9/2016 | White et al. | |
| 9,592,112 B2 | 3/2017 | Arbefeuille et al. | |
| 9,770,322 B2 | 9/2017 | Burkart et al. | |
| 9,827,123 B2 | 11/2017 | Arbefeuille et al. | |
| 9,861,503 B2 | 1/2018 | Barthold et al. | |
| 9,877,857 B2 | 1/2018 | Arbefeuille et al. | |
| 10,005,269 B2 | 6/2018 | Hall et al. | |
| 10,080,674 B2 | 9/2018 | Yuan et al. | |
| 10,299,951 B2 | 5/2019 | Arbefeuille et al. | |
| 10,390,930 B2 | 8/2019 | Arbefeuille et al. | |
| 10,617,542 B2 | 4/2020 | Chakfe et al. | |
| 10,898,357 B2 | 1/2021 | Arbefeuille et al. | |
| 11,000,359 B2 | 5/2021 | Torrance et al. | |
| 11,219,540 B2 | 1/2022 | Arbefeuille | |
| 2002/0062133 A1 | 5/2002 | Gilson et al. | |
| 2002/0177890 A1 | 11/2002 | Lenker | |
| 2002/0188344 A1 | 12/2002 | Bolea et al. | |
| 2002/0193872 A1 | 12/2002 | Trout et al. | |
| 2004/0073289 A1 | 4/2004 | Hartley | |
| 2005/0119722 A1 | 6/2005 | Styrc et al. | |
| 2005/0131518 A1 | 6/2005 | Hartley et al. | |
| 2005/0131519 A1 | 6/2005 | Hartley | |
| 2005/0131523 A1 | 6/2005 | Bashiri et al. | |
| 2006/0015171 A1 | 1/2006 | Armstrong | |
| 2006/0020319 A1 | 1/2006 | Kim et al. | |
| 2006/0184226 A1 | 8/2006 | Austin | |
| 2007/0055360 A1 | 3/2007 | Hanson et al. | |
| 2007/0135904 A1 | 6/2007 | Eidenschink et al. | |
| 2007/0213805 A1 | 9/2007 | Schaeffer et al. | |
| 2007/0233223 A1 | 10/2007 | Styrc | |
| 2008/0091260 A1 | 4/2008 | Pomeranz et al. | |
| 2008/0269867 A1 | 10/2008 | Johnson | |
| 2009/0248135 A1 | 10/2009 | Bruszewski et al. | |
| 2010/0004730 A1 | 1/2010 | Benjamin et al. | |
| 2010/0234932 A1 | 9/2010 | Arbefeuille et al. | |
| 2010/0316830 A1 | 12/2010 | Hartley et al. | |
| 2011/0190862 A1 | 8/2011 | Bashiri et al. | |
| 2011/0257720 A1 | 10/2011 | Peterson et al. | |
| 2012/0221096 A1 | 8/2012 | Roeder et al. | |
| 2012/0271401 A1 | 10/2012 | Bruszewski et al. | |
| 2012/0296360 A1 * | 11/2012 | Norris | A61F 2/97 606/191 |
| 2013/0116773 A1 | 5/2013 | Roeder et al. | |
| 2013/0116775 A1 | 5/2013 | Roeder et al. | |
| 2013/0123900 A1 | 5/2013 | Eblacas et al. | |
| 2013/0158648 A1 | 6/2013 | Hartley et al. | |
| 2013/0184806 A1 | 7/2013 | Arbefeuille et al. | |
| 2013/0245742 A1 * | 9/2013 | Norris | A61F 2/958 623/1.11 |
| 2013/0282102 A1 | 10/2013 | Peterson | |
| 2013/0289713 A1 | 10/2013 | Pearson et al. | |
| 2014/0039597 A9 | 2/2014 | Arbefeuille et al. | |
| 2014/0046428 A1 | 2/2014 | Cragg et al. | |
| 2015/0105819 A1 | 4/2015 | Becking et al. | |
| 2015/0105849 A1 | 4/2015 | Cohen et al. | |
| 2015/0202065 A1 | 7/2015 | Shalev et al. | |
| 2015/0202067 A1 | 7/2015 | Barrand et al. | |
| 2015/0272755 A1 | 10/2015 | Arbefeuille et al. | |
| 2015/0335452 A1 | 11/2015 | Rao et al. | |
| 2016/0100969 A1 | 4/2016 | Lesmeister et al. | |
| 2016/0184078 A1 | 6/2016 | Choubey et al. | |
| 2016/0199207 A1 * | 7/2016 | Treacy | A61F 2/82 623/1.12 |
| 2016/0296353 A1 | 10/2016 | Skender | |
| 2016/0302950 A1 | 10/2016 | Marmur et al. | |
| 2017/0135807 A1 | 5/2017 | Arbefeuille et al. | |
| 2017/0281382 A1 | 10/2017 | Lostetter et al. | |
| 2018/0071123 A1 | 3/2018 | Arbefeuille et al. | |
| 2019/0231571 A1 | 8/2019 | Lostetter | |
| 2019/0247178 A1 | 8/2019 | Arbefeuille | |
| 2019/0247179 A1 | 8/2019 | Lostetter | |
| 2019/0247213 A1 | 8/2019 | Lostetter | |
| 2019/0269497 A1 | 9/2019 | Arbefeuille | |
| 2019/0269498 A1 | 9/2019 | Arbefeuille et al. | |
| 2019/0282355 A1 | 9/2019 | Lostetter | |
| 2019/0328556 A1 | 10/2019 | Eubanks et al. | |
| 2019/0350694 A1 | 11/2019 | Arbefeuille et al. | |
| 2021/0100669 A1 | 4/2021 | Arbefeuille et al. | |

FOREIGN PATENT DOCUMENTS

| | | |
|---|---|---|
| EP | 1847236 A2 | 10/2007 |
| EP | 2471498 A1 | 7/2012 |
| EP | 2517672 A1 | 10/2012 |
| EP | 2735283 A1 | 5/2014 |
| EP | 2740440 A2 | 6/2014 |
| EP | 2745812 A1 | 6/2014 |
| EP | 2745813 A1 | 6/2014 |
| EP | 2749250 A1 | 7/2014 |
| EP | 2749251 A1 | 7/2014 |
| EP | 3040054 A1 | 7/2016 |
| EP | 3068339 A1 | 9/2016 |
| EP | 3078349 A1 | 10/2016 |
| EP | 3146993 A1 | 3/2017 |
| EP | 3272319 A1 | 1/2018 |
| WO | WO-97/03624 A1 | 2/1997 |
| WO | WO-99/29262 A1 | 6/1999 |

(56) References Cited

FOREIGN PATENT DOCUMENTS

| WO | WO-99/34749 A1 | 7/1999 |
| WO | WO-01/60285 A1 | 8/2001 |
| WO | WO-02/083038 A2 | 10/2002 |
| WO | WO-2005/034809 A1 | 4/2005 |
| WO | WO-2006/037086 A1 | 4/2006 |
| WO | WO-2008/130503 A2 | 10/2008 |
| WO | WO-2009/148594 A1 | 12/2009 |
| WO | WO-2010/024880 A1 | 3/2010 |
| WO | WO-2010/030370 A1 | 3/2010 |
| WO | WO-2010/127040 A1 | 11/2010 |
| WO | WO-2012/116368 A2 | 8/2012 |
| WO | WO-2012/145823 A1 | 11/2012 |
| WO | WO-2015/070792 A1 | 5/2015 |
| WO | WO-2016/122862 A1 | 8/2016 |
| WO | WO-2017/218474 A1 | 12/2017 |
| WO | WO-2018/026768 A1 | 2/2018 |

OTHER PUBLICATIONS

International Search Report and Written Opinion for International Application No. PCT/US2018/019354 dated May 7, 2018.

\* cited by examiner

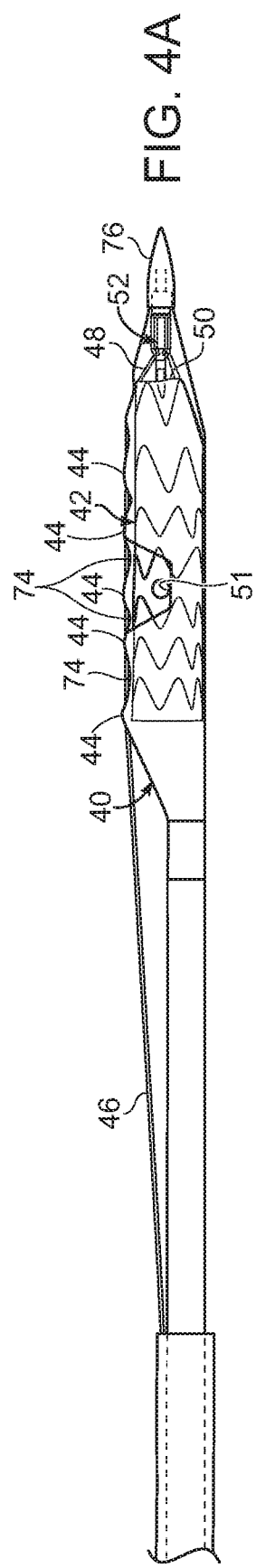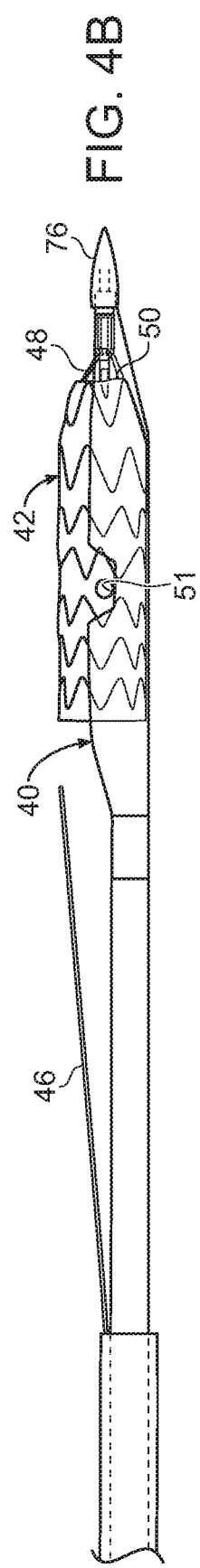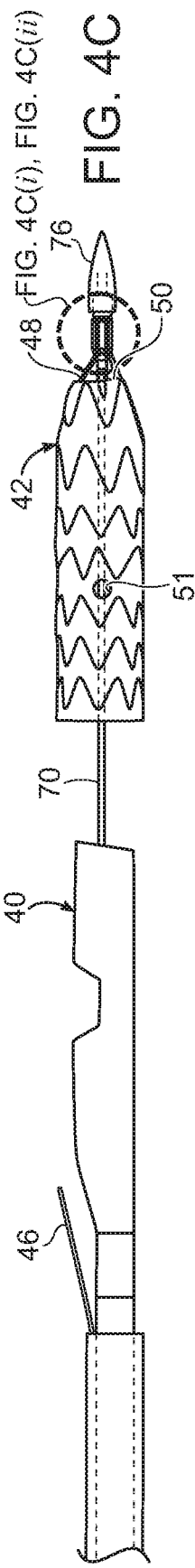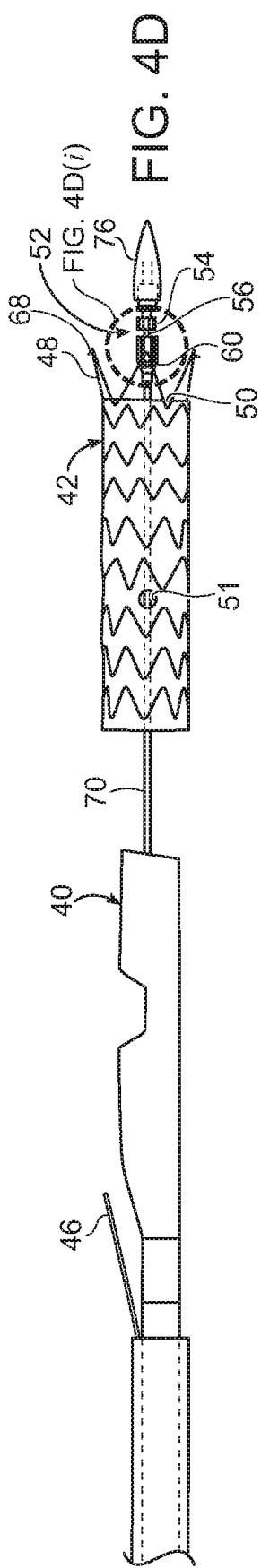

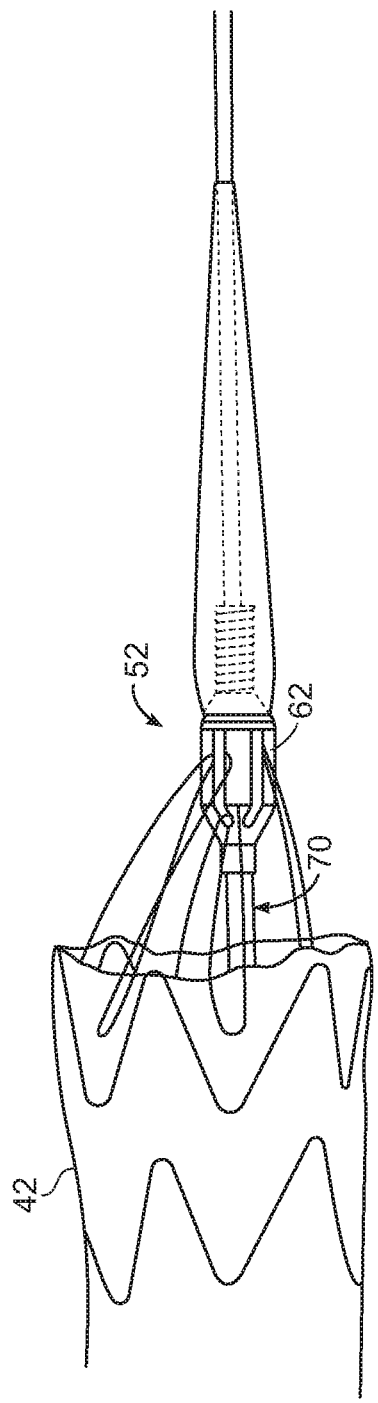
FIG. 4C(i)
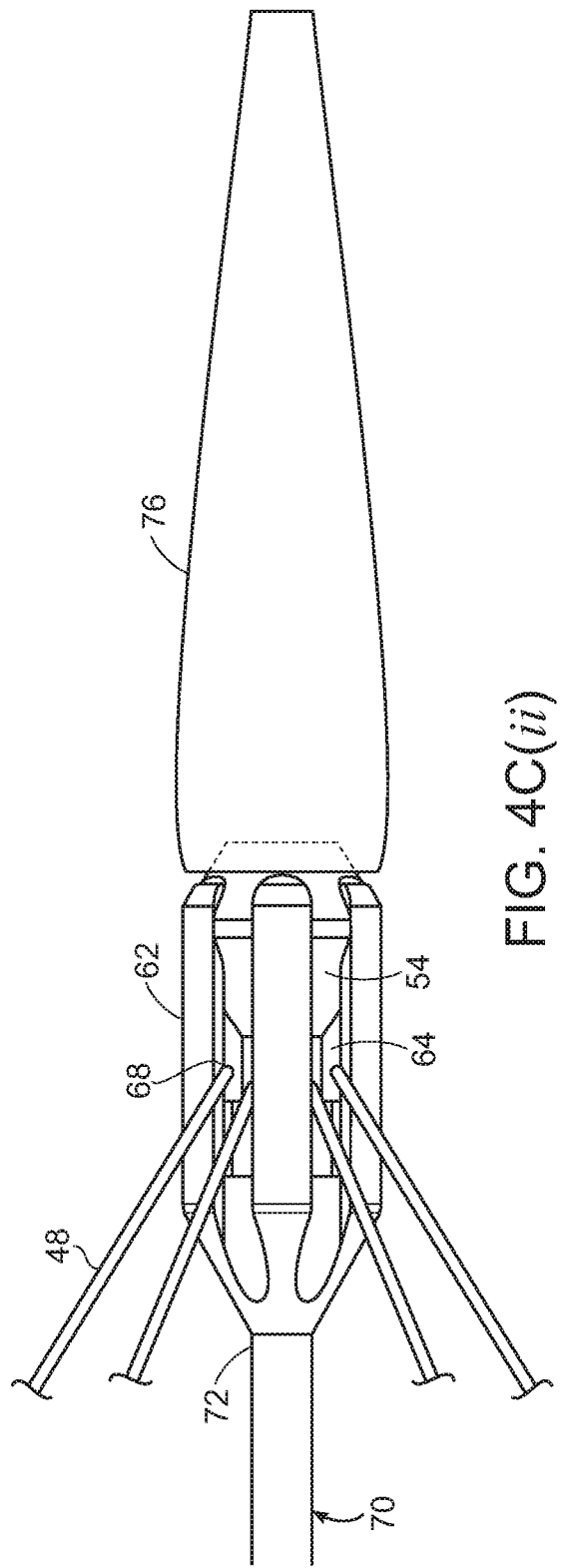
FIG. 4C(ii)

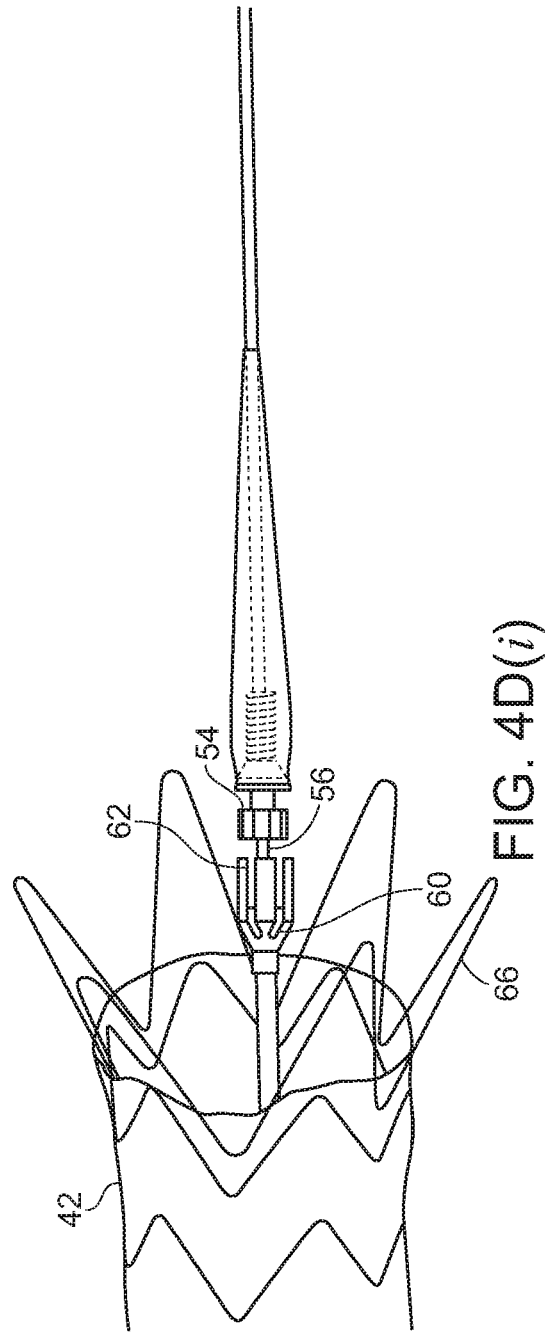

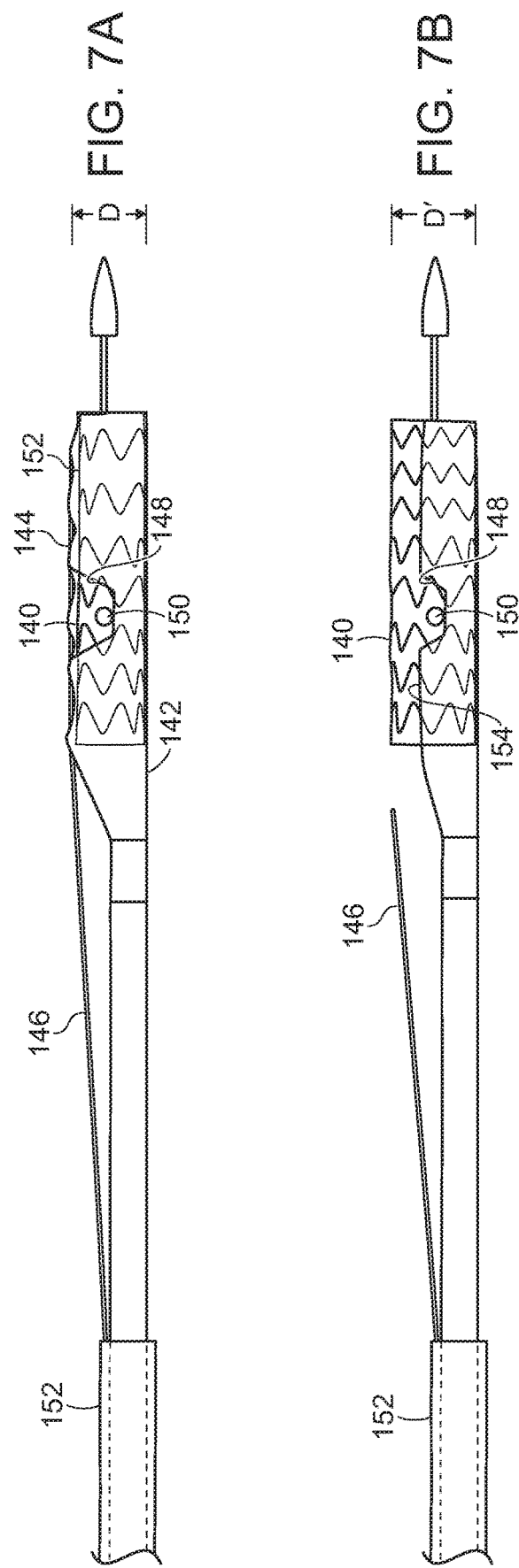

STENT GRAFT DELIVERY SYSTEM WITH CONSTRICTED SHEATH AND METHOD OF USE

RELATED APPLICATION

This application is a continuation of International Application No. PCT/2018/019354, which designated the United States and was filed on Feb. 23, 2018, published in English, which claims the benefit of U.S. Provisional Application No. 62/463,051, filed on Feb. 24, 2017. The entire teachings of the above applications are incorporated herein by reference.

BACKGROUND

Fenestrated endovascular aortic repair (FEVAR) is a minimally invasive procedure to treat aortic aneurysms that span blood vessels arising from the aorta that supply blood to vital organs including the kidneys, intestine and liver. Endovascular grafts employed in FEVAR define fenestrations for insertion of branch prostheses that serve as passageways for blood flow through arterial branches to vital organs following implantation of the endovascular graft. Maximizing blood flow to vital organs and minimizing endoleaks following repair of aneurysms with fenestrated vascular prostheses, such as juxtarenal aortic aneurysms and short-neck abdominal aortic aneurysms, present medical challenges that must be overcome if additional surgical intervention is to be avoided.

Therefore, a need exits for new and improved delivery devices, endovascular repair devices for implanting stent grafts and for methods of their use, to treat aortic pathologies, such as juxtarenal and short-neck abdominal aortic aneurysms.

SUMMARY

The present invention relates to a stent graft delivery system and a method for its use in treating and repairing arterial vascular damage, such as vascular damage associated with aortic aneurysms in regions of the aorta having arterial branches that supply blood to vital organs and tissues, including abdominal aortic aneurysms and thoracoabdominal aortic aneurysms, such as juxtarenal aortic aneurysms and short-neck abdominal aortic aneurysms.

In one embodiment, a stent graft delivery system of the invention includes a handle, a guidewire catheter, an outer catheter, a flexible sheath, and a ligature. The guidewire catheter extends distally from the handle and includes a distal end and a proximal end, and defines a longitudinal axis, the guidewire catheter being movable relative to the handle. The outer catheter is fixed to and extends distally from the handle and about the guidewire catheter. The flexible sheath extends between the guidewire catheter and the outer catheter and is longitudinally movable relative to the guidewire catheter and the outer catheter. The flexible sheath includes openings, whereby an arrangement of the openings will cause the flexible sheath to have a luminal configuration having a constricted radial diameter. The ligature extends through the openings that causes the openings to conform to the arrangement, thereby configuring the flexible sheath to conform to the constricted radial diameter of the luminal configuration, the ligature being proximally retracted from the openings to thereby release the flexible sheath from the constricted radial diameter.

In another embodiment, the invention is a method for delivering a stent graft to an aneurysm site of a patient, including the steps of directing the stent graft to an aneurysm site of the patient, the stent graft being radially constricted, at least in part, by a flexible sheath that includes openings conforming to an arrangement along a longitudinal axis of a guidewire catheter to which the stent graft is releasably fixed. The openings are released from the arrangement, whereby the stent graft is released from radial constriction, thereby delivering a stent graft to the aneurysm site.

The stent graft delivery systems and methods of the invention have several advantages. For example, the surgeon is provided with increased flexibility in the placement of the stent graft by enabling rotation or repositioning of the stent graft after it has been partially deployed while remaining in the flexible sheath, such as by only partially releasing at least one ligature extending through openings in the flexible sheath. In an embodiment wherein the stent graft includes a fenestration, the flexible sheath can also include a fenestration that is aligned with the fenestration of the stent graft, whereby the fenestration can be better aligned with a branch artery and, optionally, the proximal end of a branch prosthesis can be directed through the fenestration of the stent graft while the stent graft is radially constrained by the flexible sheath. In this embodiment, removal of the ligature releases the flexible sheath from the arrangement of openings and therefore allows the stent graft to radially expand. The flexible sheath can then be removed without interference from the implanted branch stent graft. As a consequence, a stent graft can be deployed at a surgical site with more accuracy, less risk of injury to the vasculature of the subject, and without significant risk of distorting the intended shape of the stent graft when implanted at the surgical site.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 4A is a side view of an embodiment of the stent graft delivery system of the invention, wherein a stent graft is captured by the stent graft delivery system and is radially constricted by a flexible sheath of the stent graft delivery system while openings in the flexible sheath are held in an arrangement that causes the flexible sheath to assume a luminal configuration having a constricted radial diameter, and wherein the flexible sheath defines a fenestration that is aligned with a fenestration in the stent graft.

FIG. 4B is a side view of the stent graft delivery system shown in FIG. 4A depicting radial expansion of the stent graft, while still captured by the stent graft stent graft delivery system at a proximal end, but following proximal retraction of a ligature, to release the openings of the flexible sheath from the radially constricted arrangement.

FIG. 4C is a side view of the stent graft delivery system shown in FIGS. 4A and 4B following proximal retraction of the flexible sheath to expose the stent graft during delivery to an aneurysm site.

FIG. 4C(i) is a detail of the apex capture assembly of the stent graft delivery system shown in FIG. 4C.

FIG. 4C(ii) is another detail of the apex capture assembly of the stent graft delivery system shown in FIG. 4C.

FIG. 4D is a side view of the stent graft delivery system shown in FIGS. 4A through 4C following release of a proximal bare stent of the stent graft from an apex capture assembly of the stent graft delivery system and prior to complete retraction of the stent graft delivery system from the stent graft.

FIG. 4D(i) is an apex capture assembly of the stent graft delivery system shown in FIG. 4D.

FIG. 7A is a side view of an embodiment of the stent graft delivery system of the invention, wherein a stent graft having a bare stent is radially constricted by a flexible sheath of the stent graft delivery system.

FIG. 7B is a side view of the stent graft delivery system shown in FIG. 7A following retraction of the flexible sheath.

DETAILED DESCRIPTION

The invention is generally directed to stent graft delivery systems for use in treating and repairing aortic vascular damage, such as vascular damage associated with an aortic aneurysm in regions of the aorta having arterial branches to vital organs and tissues, such as juxtarenal aortic aneurysms and short-neck abdominal aortic aneurysms.

The features and other details of the invention, either as steps of the invention or as combinations of parts of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

A description of example embodiments of the invention follows.

When reference is made herein to a prosthesis, also referred to herein as a "stent graft," "stent graft prosthesis," or "vascular prostheses," to be delivered, or implanted in a patient, the word "proximal" means that portion of the prosthesis or component of the prosthesis that is relatively close to the heart of the patient and "distal" means that portion of the prosthesis or component of the prosthesis that is relatively far from the heart of the patient. A "longitudinal axis," as that term is defined herein, means an axis along a lengthwise direction of a body that also passes through a center of gravity of the body.

When, however, reference is made to a delivery system or a component of a delivery system employed to deliver, or implant, a prosthesis, the word, "proximal," as employed herein, means closer to the clinician using the delivery system. When reference is made to a delivery system or a component of a delivery system, "distal," as that term is employed herein, means, further away from the clinician using the delivery system.

For clarity, the word "proximate" means "close to," as opposed to the meanings ascribed to "proximal" or "distal" described above with respect to either the prosthesis or a delivery system.

Figure 1A:
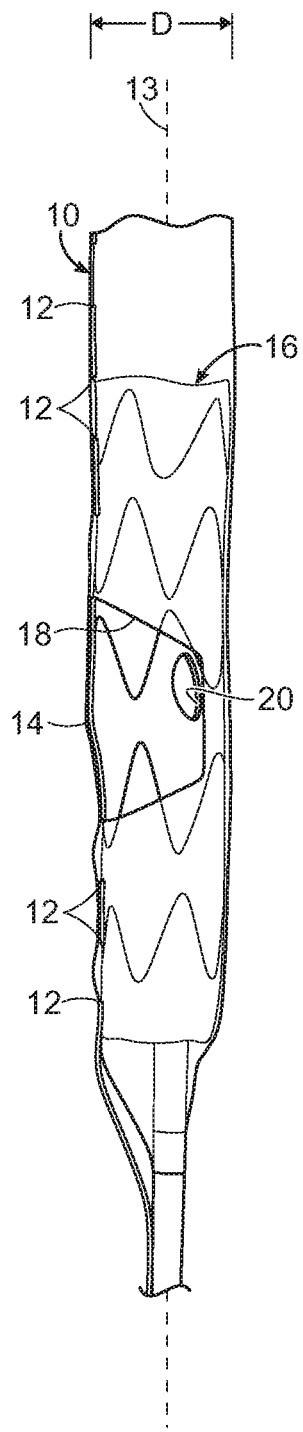
FIG. 1A is a side view of a flexible sheath of one embodiment of a stent graft delivery system of the invention, including a wire holding openings in the flexible sheath in an arrangement that causes the flexible sheath to have a luminal configuration and a constricted radial diameter, and wherein the flexible sheath defines a fenestration in the luminal configuration that is aligned with a fenestration in a stent graft radially constricted within the flexible sheath.
Figure 1B:
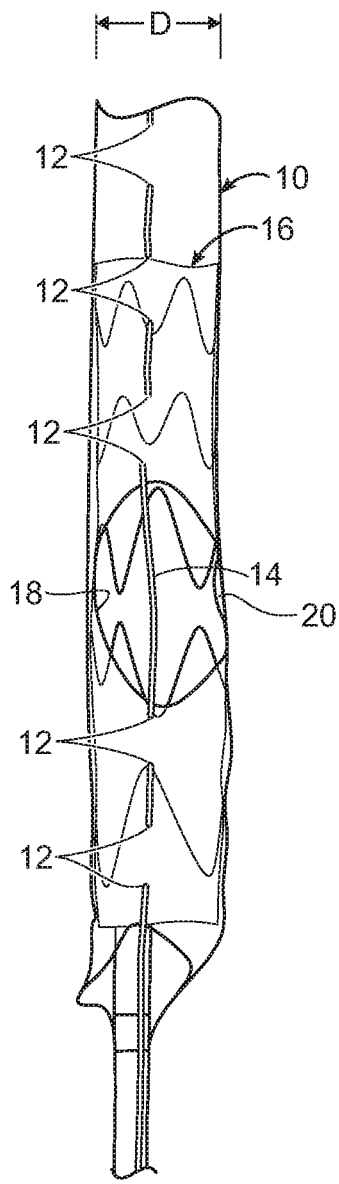
FIG. 1B is a plan view of the flexible sheath and stent graft represented in FIG. 1A.

In one embodiment, a stent graft delivery system of the invention includes a flexible sheath, as shown in FIGS. 1A and 1B. As shown in FIG. 1A, flexible sheath 10 is held in a luminal configuration by an arrangement of openings 12 that causes flexible sheath 10 to have a constricted radial diameter D. In the embodiment shown in FIG. 1A, the arrangement of openings 12 is maintained by wire 14 that extends through openings 12. Wire 14 extends generally parallel to flexible sheath 10. It is to be understood, however, that openings 12 could be arranged in any pattern that causes flexible sheath 10 to assume a luminal configuration. When openings are so arranged, regardless, stent graft 16 is maintained in a radially constricted position. In the embodiment shown in FIG. 1A, when openings 12 are arranged to cause flexible sheath 10 to have a luminal configuration having constricted diameter D, flexible sheath 10 defines fenestration 18 that exposes fenestration 20 of stent graft 16 radially constricted therein. FIG. 1B is a view of the embodiment shown in FIG. 1A, rotated 90° about longitudinal axis 13, showing wire 14 extending through openings 12 and spanning fenestration 18 of flexible sheath 10 while stent graft 16 is radially constricted within flexible sheath 10.

Examples of a suitable material for use in ligature is a wire that includes at least one member of the group consisting of a shape memory alloy, stainless steel, or a polymer, such as nylon. In one embodiment, the shape memory alloy is Nitinol. In another embodiment, ligature is a suitable thread such as is known in the art and employed to form sutures.

Figure 2A:
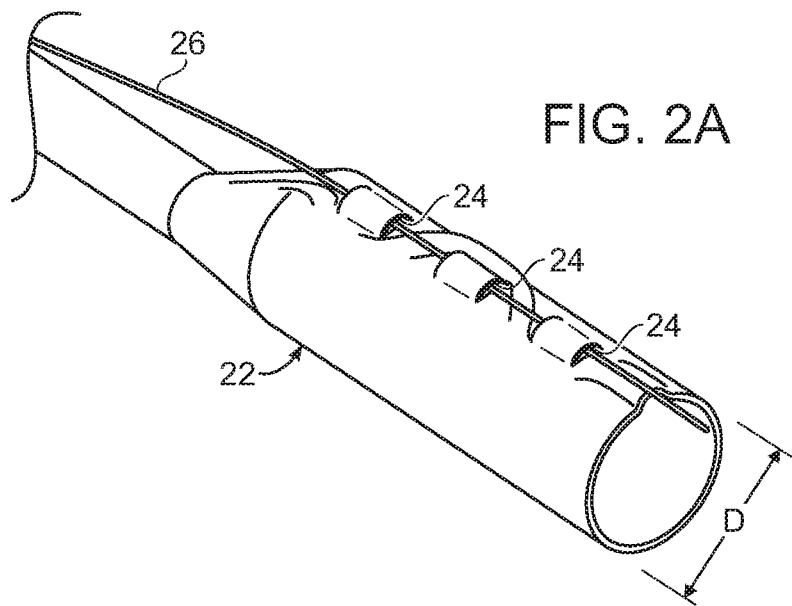
FIG. 2A is a perspective view of a flexible sheath of a stent graft stent graft delivery system of the invention having openings that, when in an arrangement by a ligature, cause the flexible sheath to have a luminal configuration having a constricted radial diameter.
Figure 2B:
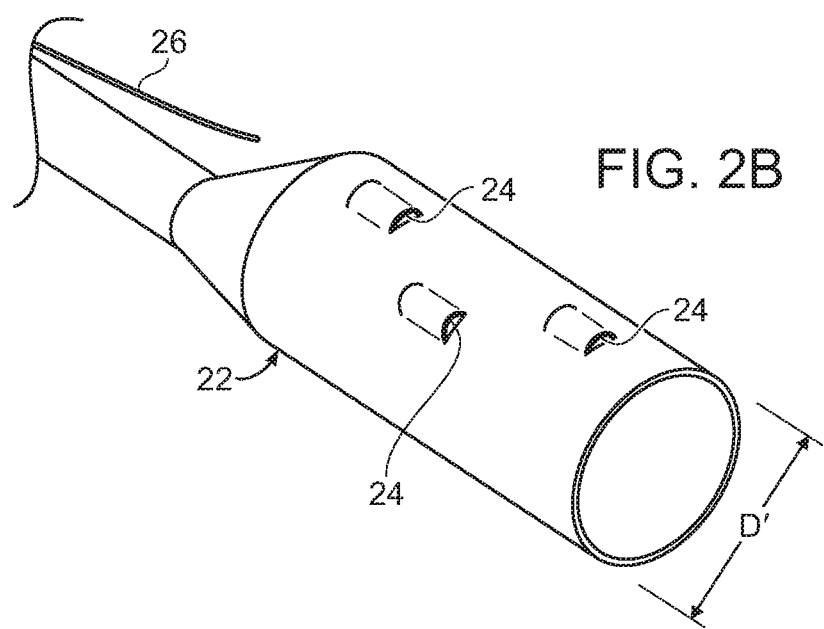
FIG. 2B is a perspective view of the embodiment shown in FIG. 2A following retraction of the ligature and consequent release of the openings of the flexible sheath from the arrangement.

FIG. 2A is a perspective view of another embodiment of a flexible sheath component 22 of the stent graft delivery system of the invention, wherein openings are slits 24 defined by flexible sheath 22 and are longitudinally aligned by wire 26 in a linear arrangement to thereby cause flexible sheath 22 to have a luminal configuration of constricted radial diameter D. FIG. 2B is a perspective view of flexible sheath 22 shown in FIG. 2A, following retraction of wire 26, thereby releasing slits 24 from the linear arrangement that causes flexible sheath to have a constricted radial diameter D. Radial expansion of flexible sheath 22, such as by radial expansion of a previously radially constricted stent graft (not shown) within flexible sheath 22 causes slits 24 to move relative to each other so they are no longer aligned in a linear arrangement, thereby causing radial diameter of flexible sheath to expand from a constricted radial diameter D to a larger radial diameter D', as shown in FIG. 2B.

Figure 3A:
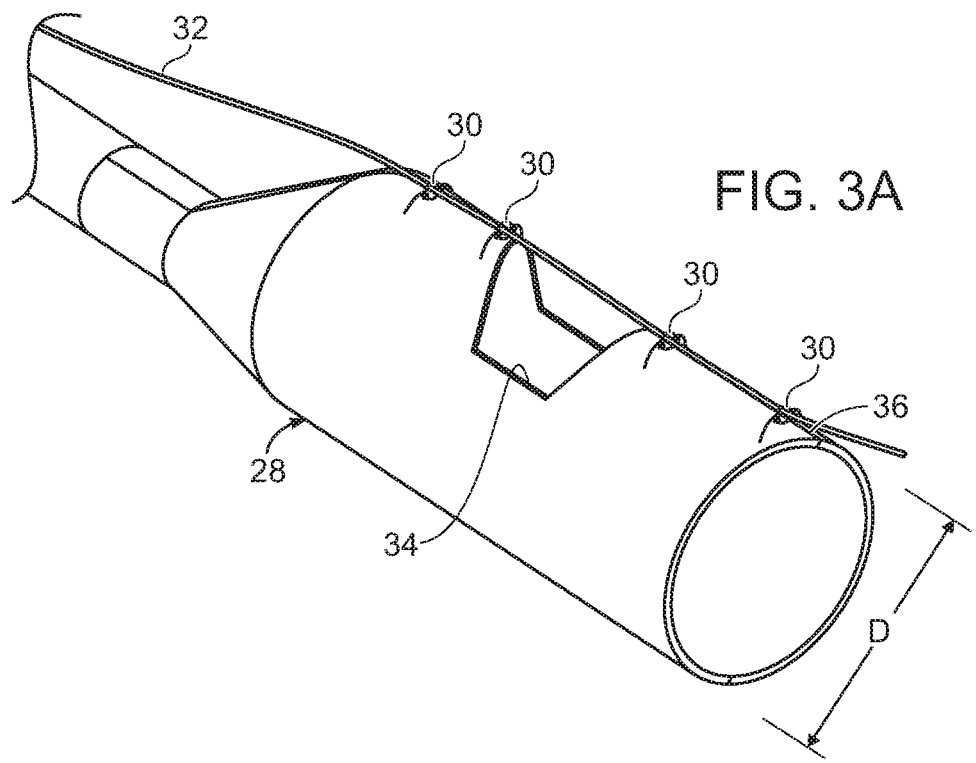
FIG. 3A is a perspective view of another embodiment of a flexible sheath of the stent graft delivery system of the invention, wherein the openings of the flexible sheath are suture loops that, when in an arrangement, cause the flexible sheath to have a luminal configuration having a constricted radial diameter, and wherein the arrangement of openings by a ligature causes scalloped edges of the flexible sheath to define a fenestration in the luminal configuration.

As shown in FIG. 3A, another embodiment of a stent graft delivery system of the invention that includes a flexible sheath 28, wherein the openings of flexible sheath 28 are suture loops 30 that, when in an arrangement, cause flexible sheath 28 to have a luminal configuration having a constricted radial diameter D. In this embodiment, the arrangement of suture loops 30 is a longitudinal alignment of suture loops by wire 32 that forms seam 36. Further, when in the luminal configuration, flexible sheath 28 defines fenestration 34.

Figure 3B:
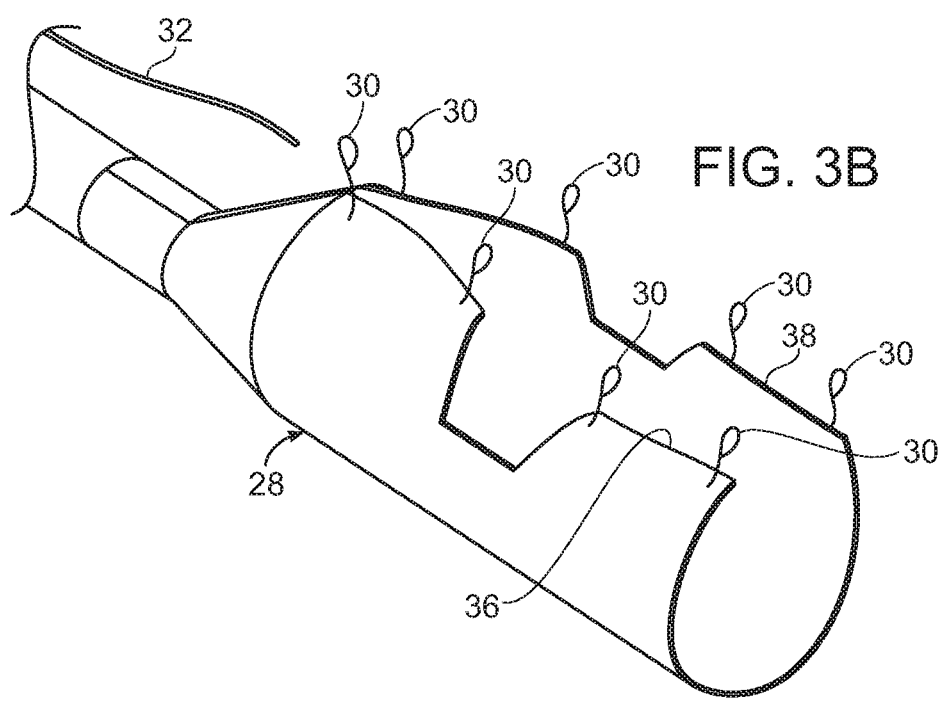
FIG. 3B is a perspective view of the embodiment shown in FIG. 3A following retraction of the ligature and consequent release of the openings from the arrangement.

FIG. 3B is a perspective view of the embodiment shown in FIG. 3A, following retraction of wire 32 from suture loops 30, whereby suture loops 30 are released from the arrangement causing flexible sheath 28 to have a luminal configuration. As further shown in FIG. 3B, seam 36 of FIG. 3A includes edges 38. Scalloped edges 38, as shown in FIG. 3B, define fenestration 34 represented in FIG. 3A, when loops 30 of flexible sheath 28 are arranged to cause flexible sheath 28 to assume a luminal configuration having constricted radial diameter D. Radial expansion of flexible sheath 28, such as by radial expansion of a self-expanding stent graft (not shown) previously radially constricted within flexible sheath 28, causes suture loops 30 to move relative to each other and opens seam 36, so that suture loops 30 and flexible sheath 28 are no longer in a radially constricted arrangement.

While the openings can be, for example, slits in the material of the flexible sheath, as shown in FIGS. 2A and 2B, the openings can also be suture loops fixed to flexible sheath, such as shown in FIGS. 3A and 3B. It is also to be understood that openings can have some other configuration, such as combinations of suture loops and slits. Further, as stated above, the arrangement of openings that cause flexible sheath to have a luminal configuration of constricted radial diameter D need not be linear, so long as the arrangement is maintained with sufficient strength to sufficiently radially constrict a stent graft for delivery to an aneurysm site of a patient.

FIGS. 4A through 4D represent successive steps in the release of a stent graft according to one embodiment of a method of the invention. As shown in FIG. 4A, flexible sheath 40 radially constricts stent graft 42 by a linear arrangement of openings 44 maintained by wire 46. Stent graft 42 includes fenestration 51 and bare stent 48 at proximal end 50 of stent graft 42 that is captured by apex capture assembly 52.

Retraction of wire 46 releases openings 44 from the linear arrangement shown in FIG. 4A, thereby enabling radial expansion of stent graft 42, such as by radial self-expansion of stent graft 42 as shown in FIG. 4B. Radial self-expansion of stent graft 42 can be effected by employing radially self-expanding stents, such as shown in the art. In one embodiment, for example, radially self-expanding stents can include struts that are joined at opposite ends to define proximal and distal apices, and can be fabricated of Nitinol, or some other shape memory alloy. Where stents are not radially self-expanding, they can be radially expanded by, for example, employing a balloon catheter, such as is known in the art.

Openings 44 previously aligned along 46 wire move as a consequence of radial expansion of stent graft 42, thereby separating edges of seam 74. Retraction of flexible sheath 40 from stent graft 42 as shown in FIG. 4C, completes exposure of stent graft 42. Proximal apices 68 of bare stent 48 are released by actuation of apex capture assembly 52, as can be seen in FIG. 4D, wherein proximal apex capture component 60 and nose cone 76 are separated from distal apex capture component 54 by proximal retraction of apex capture catheter 70, as can be seen in the transition from detailed views shown in FIGS. 4C(i) and 4C(ii) to FIG. 4D(i).

As shown in the detail of FIG. 4C(i), apex capture assembly 52 includes distal apex capture component 54 fixed to distal end 56 of guidewire catheter 58, and proximal apex capture component 60 defines tines 62, whereby distal apex capture component 54 and proximal apex capture component 60 together define a capture opening 64 that captures bare stent 48 at proximal apices 68 to thereby releasably secure and at least partially constrain proximal end 50 of stent graft 42. Apex capture catheter 70 of apex capture assembly 52 extends about guidewire catheter 58 and has a distal end 72 to which proximal apex capture component 60 is fixed. Bare stent 48 is thereby released from the stent graft delivery system.

Figure 5:
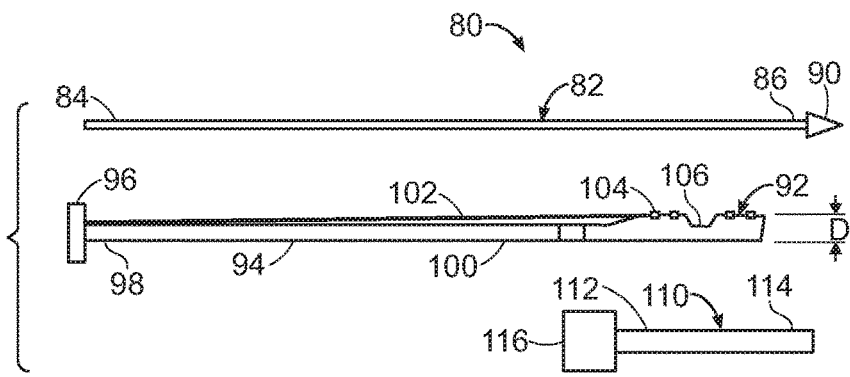
FIG. 5 is an exploded view of a stent graft delivery system of the invention.

FIG. 5 is an exploded view of one embodiment of a stent graft delivery system 80 of the invention. As shown therein, guidewire catheter 82 includes proximal end 84 and distal end 86. Nose cone 90 is fixed to distal end 86 of guidewire catheter 82. Flexible sheath 92 is secured to pushrod 94 and flexible sheath handle 96. Pushrod 94 includes proximal end 98, to which flexible sheath handle 96 is fixed, and distal end 100, to which flexible sheath 92 is fixed. Wire 102 extends through openings 104 of flexible sheath 92 and extends from flexible sheath 92 along pushrod 94 to flexible sheath handle 96. Flexible sheath 92, when wire 102 extends through openings 104, causes openings 104 to have an arrangement wherein flexible sheath 92 is in a luminal configuration and has constricted diameter D. When in a luminal configuration, scalloped edges, as shown in FIGS. 3B, and 4B through 4D form a seam, as shown in FIGS. 3A and 4A, and define fenestration 106. Introducer sheath 110 includes proximal end 112 and distal end 114. Distal handle 116 is fixed to proximal end 112 of introducer sheath 110, and releasably fixed to guidewire catheter 82.

Figure 6A:
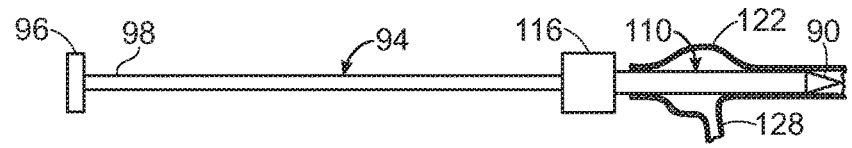
FIG. 6A is a side view of the stent graft delivery system shown in FIG. 5 when assembled, and containing a stent graft (not shown) loaded within an introducer sheath of the stent graft delivery system and having been advanced to an aneurysm to be treated by one embodiment of a method of the invention.
Figure 6B:
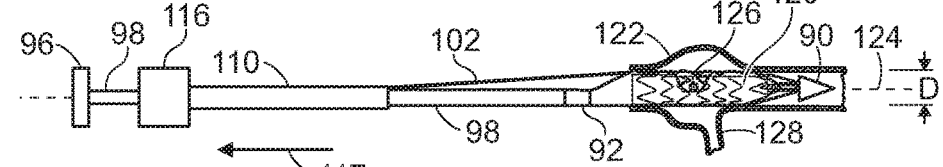
FIG. 6B is a side view of the stent graft delivery system shown in FIG. 6A after retraction of the introducer sheath to thereby expose the stent graft contained therein.

FIGS. 6A-6F represent successive stages of a method of the invention employing the assembled stent graft delivery system of FIG. 5 and loaded with stent graft prosthesis 120, such as that shown in FIGS. 4A-4D. Specifically, FIG. 6A is a side view in assembled form of stent graft delivery system 80 of FIG. 5, within which a stent graft (not shown) has been loaded and delivered to an aneurysm site 122 of a patient. Distal handle 116 and introducer sheath 110 are then retracted without being fixed to guidewire catheter 82, as shown in FIG. 6B, in the direction of arrow 117 to expose flexible sheath 92 and stent graft 120 at the aneurysm site 122. The diameter of stent graft 120 is thereby limited, at least in part, to diameter D of flexible sheath 92 prior to retraction of wire 102. In another embodiment, now shown, stent graft 120 can be delivered to aneurysm 122 by directing introducer sheath to a position distal to aneurysm 122, followed by fixing flexible sheath handle 96 to guidewire catheter 82, and advancing both in a distal direction, indicated by arrow 119, whereby stent graft 120 is advanced from introducer sheath 110 to thereby span aneurysm 122.

Figure 6C:
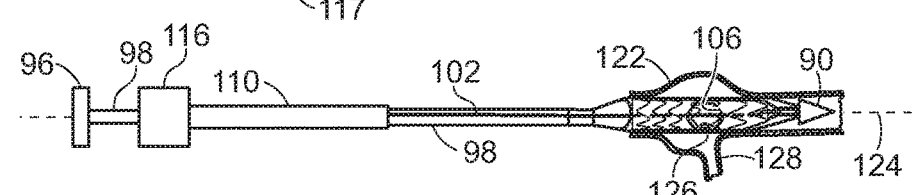
FIG. 6C is a side view of the stent graft delivery system shown in FIGS. 6A and 6B following retraction of a wire that releases the stent graft from a radially constricted position within a flexible sheath of the stent graft delivery system of the invention.
Figure 6D:
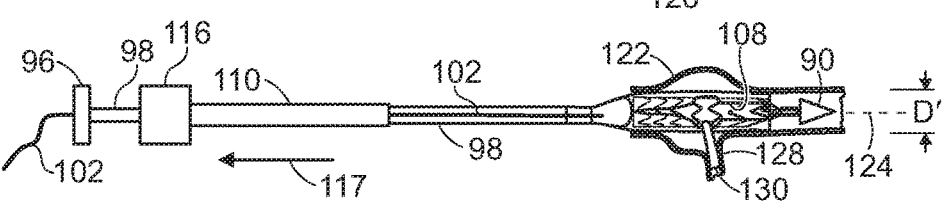
FIG. 6D is a side view of the stent graft delivery system shown in FIGS. 6A through 6C, following retraction of the flexible sheath from the stent graft still captured by an apex capture assembly of the stent graft delivery system of the invention.
Figure 6E:
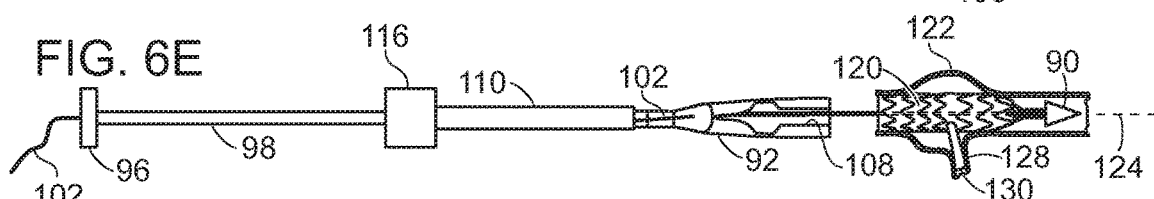
FIG. 6E is a side view of the stent graft delivery system shown in FIGS. 6A through 6D, following release of the stent graft from the apex capture assembly of the stent graft delivery system of the invention.
Figure 6F:
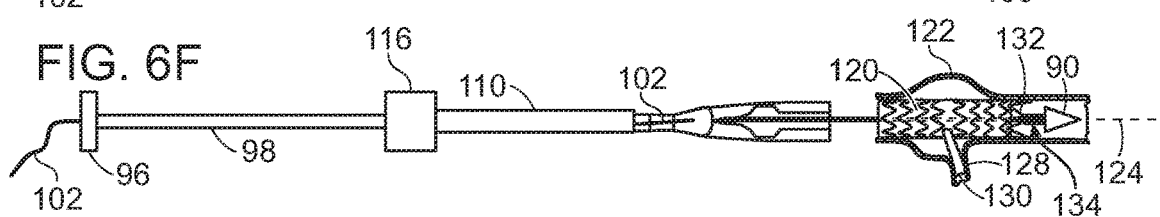
FIG. 6F is a side view of the stent graft delivery system shown in FIGS. 6A through 6E, following retraction of the stent graft delivery system from within the stent graft.
Figure 6G:
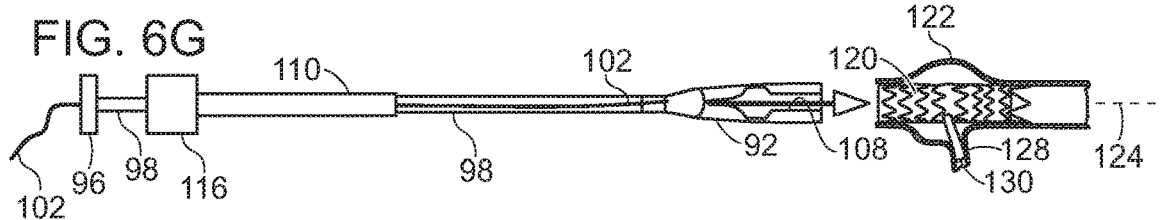
FIG. 6G is a side view of the stent graft delivery system shown in FIGS. 6A through 6F following retraction of the stent graft delivery system from within the stent graft, thereby completing implantation of the stent graft at the aneurysm by one embodiment of the invention.

As can be seen in FIG. 6C, at least guidewire catheter 82, pushrod 94 and flexible sheath 92 are axially rotated about longitudinal axis 124 to thereby align fenestration 126 of stent graft 120 and fenestration 106 of flexible sheath 92 with arterial branch 128. Branch prosthesis 130 can then be implanted in fenestration 126 of stent graft prosthesis 120 and arterial branch 128 without significant interference by flexible sheath 92. Wire 102 is retracted from openings 104 of flexible sheath 92, as shown in FIG. 6D, thereby releasing openings 104 from the arrangement, in this case a linear arrangement, that causes flexible sheath 92 to have a luminal configuration of constricted radial diameter D'. Flexible sheath handle 96 thereafter is retracted, thereby retracting pushrod 94, causing flexible sheath 92 to be separated from stent graft 120, as shown in FIG. 6E. Stent graft 120 is then released from stent graft delivery system 80 of the invention, such as by releasing bare stent 132 of stent graft prosthesis 120 from apex capture assembly 134, as shown in FIG. 6F. Distal handle is then fixed to guidewire 82, and retracted in proximal direction 117, whereby the remainder of stent graft delivery system 80 of the invention is retracted from stent graft 120, thereby completing treatment of the aortic aneurysm, as shown in FIG. 6G.

It is to be understood that implantation of a branch prosthesis through a fenestration of a stent graft prosthesis can be conducted by the same or a similar stent graft delivery system as that of the invention. It is also understood that branch prosthesis can be implanted after release of openings of the flexible sheath from the arrangement constraining the stent graft.

In another embodiment, the invention is a method for delivering a stent graft to an aneurysm site of a patient. In one embodiment, shown in FIGS. 7A and 7B, stent graft 140, which includes no bare stent is directed to an aneurysm site (not shown) of a patient, introducer sheath 152 is retracted from flexible sheath 142 and radially constricted stent graft 140. Stent graft 140 being radially constricted, at least in part, by a flexible sheath 142 that includes openings 144 conforming to an arrangement that causes the flexible sheath 142 to have a luminal configuration having a constricted radial diameter D, as shown in FIG. 7A. Openings 144 are released from the arrangement, whereby stent graft 140 is released from constraint, as shown in FIG. 7B, opening seam 152 of scalloped edge 154, thereby causing stent graft 140 to radially expand in diameter to D'. Stent graft 140 is thereby delivered to the aneurysm.

Figure 8:
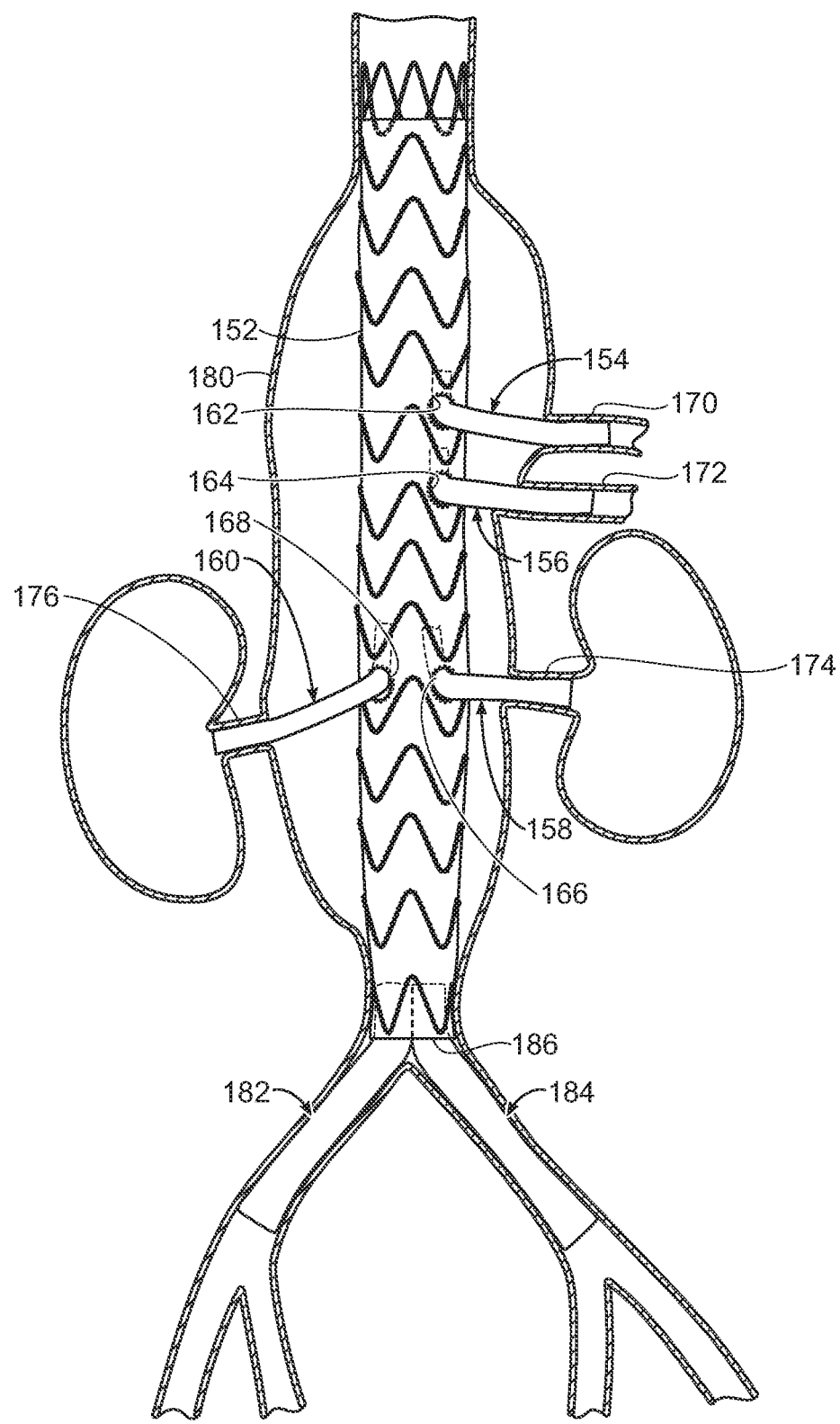
FIG. 8 is a side view of a vascular prosthesis implanted at an aneurysm in a patient employing a stent graft delivery system of the invention, and branch prostheses implanted through respective fenestrations of the vascular prosthesis and into arterial branches of the aorta.

In one embodiment, prior to release of openings 144 from the arrangement by retraction of wire 146, flexible sheath 142, defining aperture 148 and aligned with fenestration 150 of stent graft 140 is rotated to align fenestration with an arterial branch, as shown in FIG. 8, which shows one embodiment of an implanted stent graft 152 at aneurysm site 180 by use of a stent graft stent graft delivery system and method of the invention. Thereafter, branch prostheses 154, 156,158,160 can be directed through fenestrations 162,164, 166,168 of stent graft 152 to respective arterial branches 170,172,174,176, shown in FIG. 8. Leg stent graft prostheses 182,184 extend from distal end 186 of stent graft 180.

Although not shown, the distal end of the vascular repair device of the invention can be bifurcated and additional prostheses can be implanted into the distal end of the bifurcated vascular prosthesis.

Vascular prostheses implanted by the stent graft systems and methods of the invention can be implanted, for example, by transfemoral access. Additional branch prostheses that are directed into the vascular prostheses of the invention can be implanted, for example, by supraaortic vessel access (e.g., through the brachial artery), or by transfemoral access, or access from some other branch or branch of major blood vessels, including peripheral blood vessels.

The teachings of all patents, published applications and references cited herein are incorporated by reference in their entirety. The relevant teachings of U.S. Pat. Nos. 8,292,943; 7,763,063; 8,308,790; 8,070,790; 8,740,963; 8,007,605; 9,320,631; 8,062,349; 9,198,786; 8,062,345; 9,561,124; 9,173,755; 8,449,595; 8,636,788; 9,333,104; 9,408,734; 9,408,735; 8,500,792; 9,220,617; 9,364,314; 9,101,506; 8,998,970; 9,554,929; 9,439,751; 9,592,112; 9,655,712, 9,827,123, 9,877,857, 9,907,686; U.S. patent application Ser. Nos. 14/575,673; 15/166,818; 15/167,055; 14/272,818; 14/861,479; 15/478,424; 15/478,737; 15/587,664; 15/604, 032; 15/672,404; 15/816,772; 15/839,272; 15/417,467; PCT/US2017/025844; PCT/US2017/025849; PCT/US2017/ 025912; PCT/US2017/034223 and PCT/US2017/046062, are also incorporated by reference in their entirety.

The relevant teachings of International Application Numbers: PCT/US2018/019355; PCT/US2018/019344; PCT/ US2018/019349; PCT/2018/019353; PCT/US2018/019352; PCT/US2018/019342; PCT/US2018/019350; PCT/US2018/ 019356; PCT/US2018/019351; and PCT/2018/019510 are also incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A stent graft delivery system, comprising:
 a) a handle;
 b) a guidewire catheter extending distally from the handle and having a distal end and a proximal end, and defining a longitudinal axis, the guidewire catheter being moveable relative to the handle;
 c) an outer catheter fixed to and extending distally from the handle and about the guidewire catheter;
 d) a flexible sheath extending between the guidewire catheter and the outer catheter and longitudinally moveable relative to the guidewire catheter and the outer catheter, wherein the flexible sheath defines a plurality of pairs of transverse slits, wherein each pair of transverse slits is arranged longitudinally and defines a longitudinal pathway between the transverse slits of each pair of transverse slits, whereby longitudinal alignment of the longitudinal pathways defined by the plurality of pairs of transverse slits in a linear arrangement will cause the flexible sheath to have a luminal configuration having a constricted radial diameter, wherein the luminal configuration has an expanded radial diameter when the longitudinal pathways defined by the plurality of pairs of transverse slits are not longitudinally aligned in the linear arrangement, the expanded radial diameter being greater than the constricted radial diameter of the flexible sheath when the longitudinal pathways defined by the plurality of pairs of transverse slits are longitudinally aligned in the linear arrangement, and wherein the flexible sheath has a continuous circumference in the luminous configurations of both the expanded and the constricted radial diameters; and e) a ligature extending through the plurality of pairs of transverse slits, wherein the ligature extends within the flexible sheath between each pair of the plurality of pairs of slits, thereby causing the longitudinal pathways defined by the plurality of pairs of transverse slits to conform to the longitudinal alignment in the linear arrangement, thereby configuring the flexible sheath to conform to the constricted radial diameter of the luminal configuration, the ligature being proximally retractable from the plurality of pairs of transverse slits to thereby release the flexible sheath from the constricted radial diameter.

2. The delivery system of claim 1, wherein the ligature is a thread, whereby the longitudinal pathways defined by the plurality of pairs of transverse slits are aligned by tension on the thread.

3. The delivery system of claim 1, wherein the ligature is a wire.

4. The delivery system of claim 3, wherein the wire includes at least one member of the group consisting of a shape memory alloy, stainless steel, and a polymer.

5. The delivery system of claim 4, wherein the shape memory alloy includes Nitinol.

6. The delivery system of claim 4 wherein the polymer includes nylon.

7. The delivery system of claim 1, further including a stent graft prosthesis within the flexible sheath, the stent graft including: a) a proximal end at the distal end of the guidewire catheter, a distal end, and a wall extending about the guidewire catheter, and b) a plurality of stents fixed to and distributed along the wall of the stent graft, wherein the stent graft is radially constricted when the longitudinal pathways defined by the plurality of pairs of transverse slits of the flexible sheath are aligned.

8. The delivery system of claim 7, wherein the stent graft further includes a bare stent at the proximal end of the stent graft, the bare stent including struts that define proximal apices.

9. The delivery system of claim 8, further including an apex capture assembly that releasably captures the proximal apices of the bare stent.

10. The delivery system of claim 9, wherein the apex capture assembly includes a distal apex capture component fixed to the distal end of the guidewire catheter, a proximal apex capture component whereby the distal and proximal apex capture component together define a capture opening that captures the proximal apices of the bare stent to thereby releasably capture and at least partially constrain the proximal end of the stent graft, and an apex capture catheter extending about the guidewire catheter and having a distal end to which the proximal apex capture component is fixed, whereby the proximal apices of the bare stent and, consequently, the proximal apex capture component can be released when the apex capture catheter is retracted from the distal apex capture component.

11. A method for delivering a stent graft prosthesis to an aneurysm site of a patient, comprising the steps of:
   a) directing the stent graft to the aneurysm site of the patient by a delivery system, the delivery system including,
      i) a handle,
      ii) a guidewire catheter extending distally from the handle and having a distal end and a proximal end, and defining a longitudinal axis, the guidewire catheter being moveable relative to the handle,
      iii) an outer catheter fixed to and extending distally from the handle and about the guidewire catheter,
      iv) a flexible sheath extending between the guidewire catheter and the outer catheter and longitudinally moveable relative to the guidewire catheter and the outer catheter, wherein the flexible sheath defines a plurality of pairs of transverse slits, wherein each pair of transverse slits is arranged longitudinally and defines a longitudinal pathway between the transverse slits of each pair of transverse slits, whereby longitudinal alignment of the longitudinal pathways defined by the plurality of pairs of transverse slits in a linear arrangement will cause the flexible sheath to have a luminal configuration having a constricted radial diameter, wherein the luminal configuration has an expanded radial diameter when the longitudinal pathways defined by the plurality of pairs of transverse slits are not longitudinally aligned in the linear arrangement, the expanded radial diameter being greater than the constricted radial diameter of the flexible sheath when the longitudinal pathways defined by the plurality of pairs of transverse slits are longitudinally aligned in the linear arrangement, and wherein the flexible sheath has a continuous circumference in the luminous configurations of both the expanded and the constricted radial diameters, and
      v) a ligature extending through the plurality of pairs of transverse slits, wherein the ligature extends within the flexible sheath between each pair of the plurality of pairs of slits, thereby causing the longitudinal pathways defined by the plurality of pairs of transverse slits to conform to the longitudinal alignment in the linear arrangement, thereby configuring the flexible sheath to conform to the constricted radial diameter of the luminal configuration, the ligature being proximally retractable from the plurality of pairs of transverse slits to thereby release the flexible sheath from the constricted radial diameter; and
   b) releasing the longitudinal pathways defined by the plurality of pairs of transverse slits from the longitudinal alignment, whereby the stent graft is released from radial constriction by the flexible sheath, thereby delivering the stent graft to the aneurysm site.

12. The method of claim 11, wherein the step of releasing the longitudinal pathways from the longitudinal alignment includes retracting the ligature from the longitudinal pathways.

* * * * *